United States Patent
Krishnan et al.

(10) Patent No.: US 7,871,408 B2
(45) Date of Patent: Jan. 18, 2011

(54) METHODS AND SYSTEMS FOR GATED OR PULSED APPLICATION OF ABLATIVE ENERGY IN THE TREATMENT OF CARDIAC DISORDERS

(75) Inventors: Subramaniam Krishnan, Newport Beach, CA (US); Kalyanam Shivkumar, Los Angeles, CA (US); Suresh Rathnam, Hyderabad (IN)

(73) Assignee: Henry Ford Health System, Detroit, MI (US)

( * ) Notice: Subject to any disclaimer, the term of this patent is extended or adjusted under 35 U.S.C. 154(b) by 995 days.

(21) Appl. No.: 11/259,881

(22) Filed: Oct. 27, 2005
(Under 37 CFR 1.47)

(65) Prior Publication Data

US 2006/0200118 A1 Sep. 7, 2006

Related U.S. Application Data

(60) Provisional application No. 60/623,046, filed on Oct. 28, 2004.

(51) Int. Cl.
*A61B 18/18* (2006.01)
(52) U.S. Cl. .............................. 606/32; 606/27; 606/33; 606/41
(58) Field of Classification Search .................. 606/32, 606/41, 45; 128/898
See application file for complete search history.

(56) References Cited

U.S. PATENT DOCUMENTS

| | | | |
|---|---|---|---|
| 4,936,281 A | 6/1990 | Stasz | |
| 5,125,926 A | 6/1992 | Rudko et al. | |
| 6,286,512 B1 * | 9/2001 | Loeb et al. | 128/898 |
| 6,287,297 B1 | 9/2001 | Woodruff et al. | |
| 6,468,271 B1 | 10/2002 | Wentzel et al. | |
| 6,666,862 B2 | 12/2003 | Jain et al. | |

OTHER PUBLICATIONS

PCT International Search Report for PCT/US05/38864, 2 pages.

* cited by examiner

*Primary Examiner*—Lee S Cohen
(74) *Attorney, Agent, or Firm*—Rader, Fishman & Grauer PLLC; James F. Kamp

(57) ABSTRACT

The present invention comprises methods and systems for treating a cardiac arrhythmia in a mammal by administering gated or pulsed radiofrequency current or other ablative energy to the mammal during one or more time periods of increased coronary blood flow. Preferred embodiments of the invention comprise, without limitation, the gated or pulsed administration of radiofrequency current in association with the formation of the dicrotic notch in the arterial blood pressure curve of the mammal. In accordance with the invention, the thermal effects of ablative energy application on the coronary artery are avoided or mitigated due to rapid coronary blood flow resulting in heat loss and minimization of damage to blood vessels.

11 Claims, 3 Drawing Sheets

Example of 1:2 IABP support and RF gated to IABP inflation

METHODS AND SYSTEMS FOR GATED OR PULSED APPLICATION OF ABLATIVE ENERGY IN THE TREATMENT OF CARDIAC DISORDERS

CROSS-REFERENCE TO RELATED APPLICATIONS

This application claims priority based on U.S. Provisional Patent Application No. 60/623,046, filed Oct. 28, 2004, which is hereby incorporated by reference in full.

FIELD OF THE INVENTION

The present invention relates to the field of methods for treatment of electrophysiological disorders of the mammalian heart and treatment of disorders of the liver, uterus and other organs.

BACKGROUND

The mammalian heartbeat is stimulated by electric signals within the heart muscle. The heart usually beats in a steady rhythm. However, cardiac arrhythmias are common abnormalities in the rhythm of the heart beat where the heart may beat very fast ("tachycardia") or very slow ("bradycardia"). Arrthymias may arise when electrical impulses in the heart's electrical network travel irregular pathways or repeat the same pathways over and over.

Arrhythmias are often associated with problems in micro or macro anatomical zones in heart tissue. Arrhythmias may result from the development of an improper electrical circuit caused by a developmental anomaly or a myocardial scar. Treatment sometimes involves altering those tissues. The destruction of these tissues and any other abnormal electrical circuits is called ablation therapy.

Ablation is a procedure to restore normal rhythm by destroying very small, carefully selected parts of the heart that cause arrhythmias. Ablation can be performed either by catheters or during heart surgery.

One method of ablation is radiofrequency ("RF") catheter ablation, in which RF current is applied to the treatment zone via a blood vessel or directly on the inner or outer surface of the heart. RF ablation came into clinical practice at the end of the 1980's and has revolutionized the treatment of patients with abnormal heart rhythms.

In RF ablation, necrosis or scar tissue in pathologic tissue is induced, thus reorienting the electrical transmission in the heart and alleviating the arrhythmia. In this technique, a site of abnormal impulse formation or a critical part of the arrhythmic pathway may be located, for example, by cardiac activation mapping during the arrhythmia. RF energy can be applied to the area, resulting in the destruction of a small portion of critical tissue and alleviation of the arrhythmia for the patient.

In RF catheter ablation, a clinician (typically an electrophysiologist) may introduce a cardiac catheter into the chambers of the heart via the peripheral vasculature. An electrode is mounted on the end of the catheter through which RF current from an RF generator is passed with proper grounding and siting of the catheter. The passage of current most often produces a localized lesion that alters electrical pathways but does not affect cardiac function.

However, application of RF techniques is not without complication or contraindications in certain patient populations. As some examples, catheter ablation of some arrhythmias may require application of RF current in the vicinity of coronary arteries. Application of the current generates heat, which can damage adjacent blood vessels. This inherently increases the risk of damage to the coronary arteries due to the proximity of the coronary arteries to the ablation sites of accessory pathways. With RF ablations performed in the vicinity of coronary arteries, susceptibility to damage is inversely proportional to vessel diameter. It is also known to those of ordinary skill in the art that damage to the coronary arteries can occur from ablation performed with energy sources other than radiofrequency current, including without limitation, microwave, ultrasound, or high intensity focused ultrasound ("HIFU") energy.

Moreover, obstruction of the right coronary artery as a late sequela after RF application to the tricuspid annulus has been previously described in an animal model. It has also been inferred that catheter ablation in humans targeting accessory pathways in the right free wall may damage the right coronary artery. In similar fashion, stenosis of the coronary artery is a substantial risk of RF current application in children and although rare, catheter ablation of atrial flutter has also been associated with acute thrombotic occlusion of the right coronary artery. A risk of damage to the coronary arteries remains in some regions, as one example only, in the ostium of the middle cardiac vein, and in children.

Thus, an unmet need exists for methods of controlling or alleviating cardiac arrhythmias while decreasing the risks of complications from the application of RF current or other sources of ablative energy.

SUMMARY OF THE INVENTION

The present invention meets this unmet need by comprising methods and systems for treating a cardiac arrhythmia in a mammal by administering gated or pulsed radiofrequency current or types of energy to the mammal during one or more time periods of increased coronary blood flow. Preferred embodiments of the invention comprise, without limitation, the administration of radiofrequency current in association with the formation of the dicrotic notch in the arterial blood pressure curve of the mammal or other fiducial markers of diastole, including without limitation, electrical diastole (from the down slope of the T-wave to the peak of the QRS complex). In accordance with the invention, the thermal effect of RF current application on the coronary artery is avoided or mitigated due to rapid coronary blood flow resulting in heat loss and minimization of damage to blood vessels. In addition, in some embodiments, without limitation, the thermal effects of ablative energy are mitigated or avoided by administering timed or gated ablative energy in relation to time periods of increased blood flow that maximize the heat sink effect in determinable locations on or within the mammal.

Other aspects of the invention will be apparent to those skilled in the art after reviewing the drawings and the detailed description below.

BRIEF DESCRIPTION OF THE DRAWINGS

The present invention will now be described, by way of example, with reference to the accompanying drawings, in which.

Figure 1:
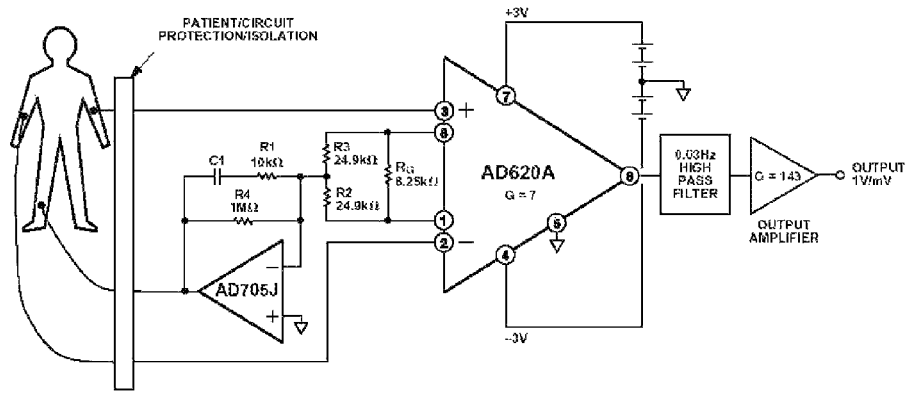
FIG. 1 is a sample diagram of a medical electrocardiogram monitor circuit.

Other aspects of the invention will be apparent to those skilled in the art after reviewing the detailed description below.

DETAILED DESCRIPTION

In some preferred embodiments, without limitation, the present invention comprising methods of treating a cardiac arrhythmia in a mammal by administering gated or pulsed radiofrequency current or other types of ablative energy to the mammal during at least one time period of increased coronary blood flow. Preferred embodiments of the invention comprise, without limitation, the administration of radiofrequency current in association with the formation of the dicrotic notch in the arterial blood pressure curve of the mammal or other fiducial markers of diastole, including without limitation, electrical diastole (from the down slope of the T-wave to the peak of the QRS complex). In accordance with the invention, the thermal effect of RF current application on the coronary artery are avoided or mitigated due to rapid coronary blood flow resulting in heat loss and minimization of damage to blood vessels.

The rate and amount of coronary blood flow is known to change during the cardiac cycle. In the normal left ventricle, the largest fraction of total coronary blood flow occurs during diastole. Left coronary blood flow is thought to cease at a perfusion pressure of about 80 mmHg. At the onset of isovolumic relaxation, coronary inflow rapidly increases to a peak value and then gradually decreases as it follows the pattern of the aortic pressure curve.

Coronary blood flow may act as a heat sink during application of RF current or other energy types, including without limitation, microwave, ultrasound, or HIFU energy. The heat sink effect of the epicardial coronary arteries is thought to be fortuitously self-protective. The high rate of flow in the coronary arteries most likely prevents any substantial heating of the vascular endothelium even when the RF electrode is positioned close to the vessel. Although the effect of convective cooling by coronary arteries has not been measured in vivo, reports of extensive modeling in other experimental systems support this hypothesis.

This heat sink effect likely accounts for the paucity of reported coronary arterial complications or measurable changes in coronary arteriograms performed before and after RF catheter ablations. With RF ablation performed in the vicinity of coronary arteries, the overt vascular injury is restricted to smaller vessels. This is likely because larger vessels are protected by a greater blood flow due to the heat sink effect.

We have discovered unexpectedly that the heat sink effect of blood flow may support the application of gated or pulsed RF current or other ablative energy in order to alleviate or minimize the risk of damage to coronary vessels during RF ablation, and/or damage to other tissues associated with the application of ablative energy. In accordance with the invention, the phenomenon of blood flow acting as a heat sink supports the selective application of RF current only during diastole or associated times when blood flow through the coronary vessels is at its maximum, thus minimizing or eliminating the risk of damage to the coronary vessels due to RF application. The application time may also be adjusted in order to apply the ablative energy in association with increased blood flow to other tissues, organs, or other locations of interest.

The normal electrocardiogram is composed of a P wave, a QRS complex, and a T wave, which represent phases of the heart beat during which the atria and ventricles of the heart are discharging and repolarizing in order to stimulate the heart tissue. The P wave represents atrial depolarization, and the QRS complex represents ventricular depolarization. The T wave reflects the phase of rapid repolarization of the ventricles and can be associated with the onset of high coronary blood flow. A typical tracing of the T wave corresponds to the dicrotic notch of the pressure tracing, which reflects the transient increase in arterial blood pressure that corresponds to the closing of the aortic (semilunar) valve. When the valve closes, vibrations are created, causing a small bump on the arterial pressure tracing, where it would normally be decreasing. Circuitry for monitoring electrocardiograms and pressure tracings are well known to those of ordinary skill in the art (as one example only, without limitation, see FIG. 1.)

Figure 2:
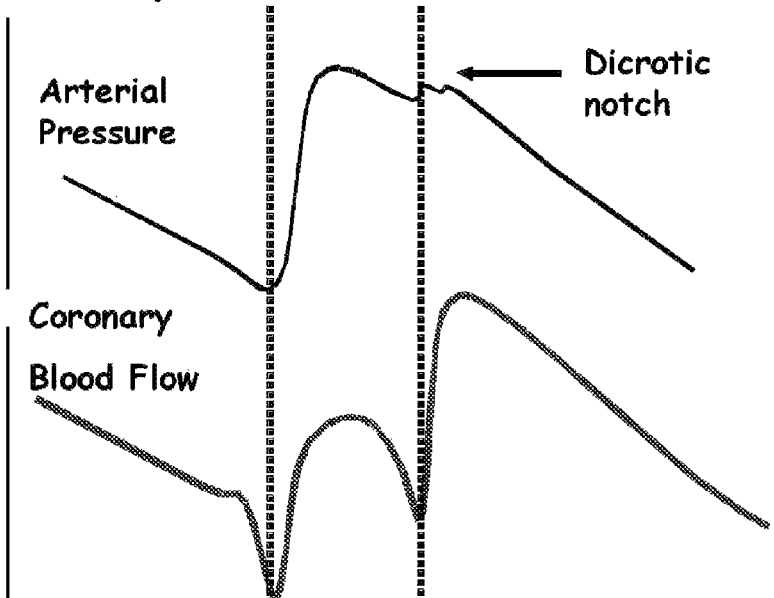
FIG. 2 is a graph of coronary blood flow and arterial blood pressure versus time.
Figure 3:
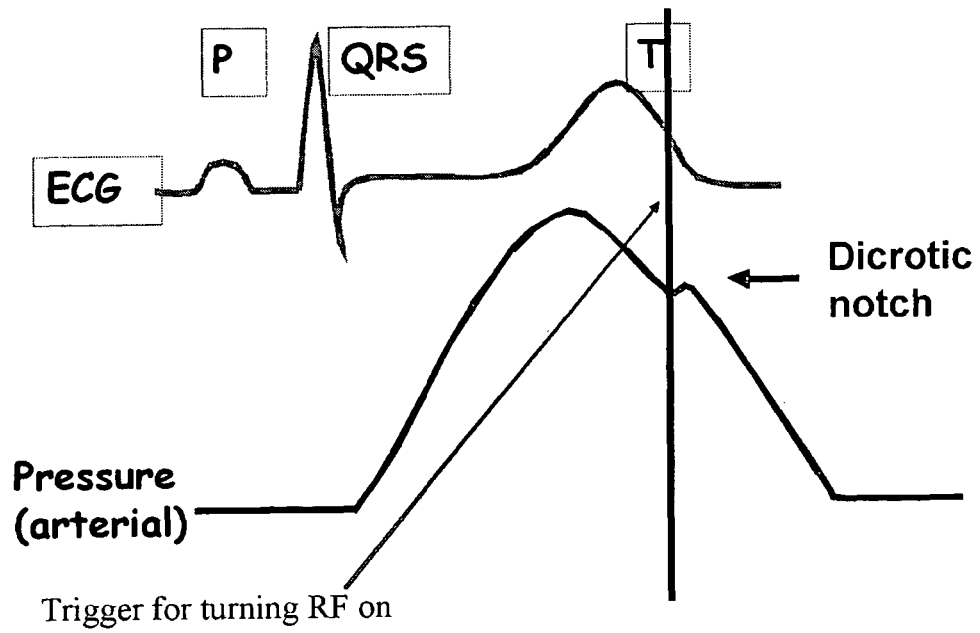
FIG. 3 is a graph of simultaneous ECG and arterial blood pressure recordings versus time.

As shown in FIG. 2, coronary blood flow increases dramatically during the time period associated with the formation of the dicrotic notch in the corresponding curve of arterial blood pressure. Thus, in some embodiments, without limitation, the RF current or other energy is gated or pulsed to be turned on in conjunction with the timing of the dicrotic notch (FIG. 3).

Figure 4:
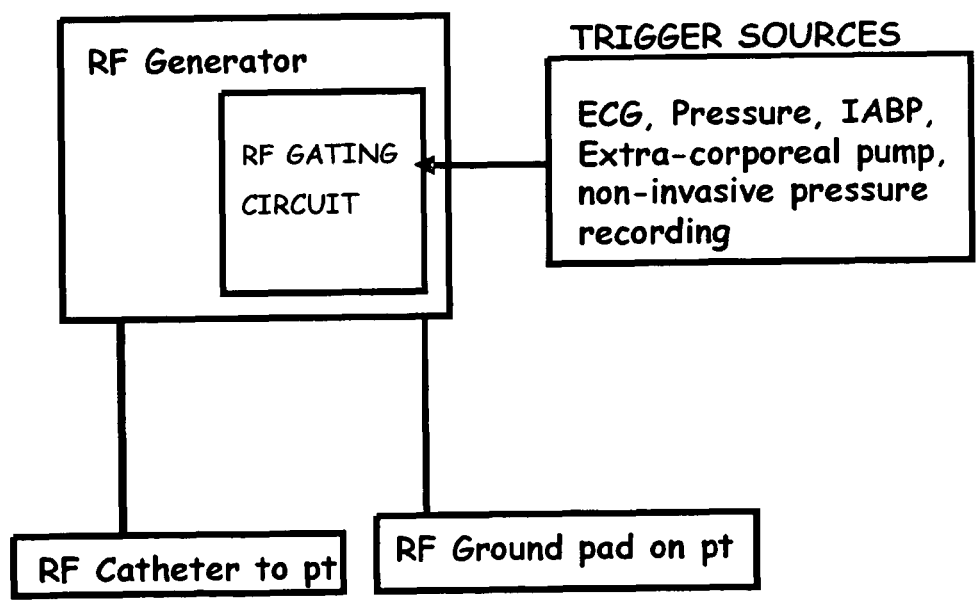
FIG. 4 is a schematic diagram showing one embodiment of pulsed RF input and delivery, without limitation.

FIG. 4 show a schematic diagram of pulsed RF input triggers and delivery to a mammal. In some embodiments, the invention comprises a source of RF energy, such as an RF generator. Although RF energy is described as an exemplary embodiment, the invention also comprises any other type and/or source of ablative energy known to those of ordinary skill, including without limitation, microwave, ultrasound, or HIFU energy. The generator has means of gating or pulsing the delivering of RF energy; such means are known to those of ordinary skill in the art. The gating or pulsing of the RF energy may be triggered by signals derived from an ECG, pressure reading, intraarterial balloon pump ("IABP") or extracorporeal pump operation, non-invasive pressure recording, or other source which permits the detection of the rise in coronary blood flow during the heart beat cycle. The RF energy is thus delivered to the subject by means of an RF catheter and ground, or other apparatus or means known to those of ordinary skill.

Figure 5:
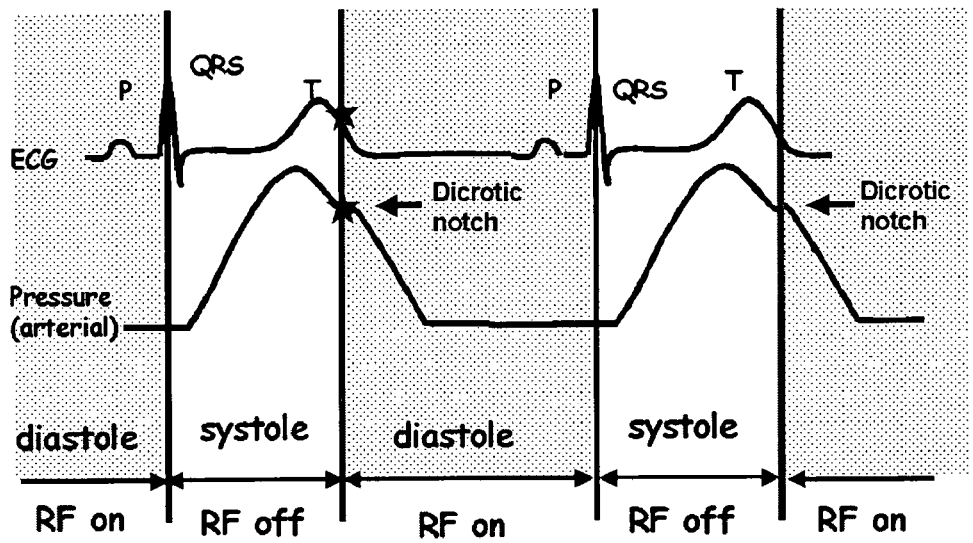
FIG. 5 is a diagram of pulsed RF gated to ECG and arterial blood pressure.

High volume or rapid displacement of blood in the blood vessel can act as a protective heat sink. In conjunction with this phenomenon, the invention comprises the coordinated application of RF current with the diastolic period in the heart beat when blood flow is highest. Thus, the invention comprises the use of coordinated monitoring and circuiting in order to monitor the PQRST complex and to trigger the RF current during the "T" wave and thereby coordinate application of the current with rapid blood flow in the vessel (see e.g., FIG. 5). The current is typically turned off in proximity with the onset of the QRS complex. Thus, the invention comprises the coordination of detection of the correct phase of the ECG signal with the gated and controlled application of the RF current, and perhaps other factors.

Pulsed or gated delivery of the RF current in conjunction with the formation of the dicrotic notch takes advantage of the convective cooling of the tissue by increased blood flow during diastole. In addition, one can also intentionally increase blood flow with an IABP, which uses gating techniques to increase balloon inflation during diastole.

The IABP is a mechanical aid to the circulatory function of the heart. The basic components of the device are often a catheter tipped with a balloon and a pump machine that inflates the balloon with either helium or carbon dioxide. The balloon is inserted via a femoral artery and is guided into position in the descending thoracic artery. The balloon is then inflated and deflated as desired via a pump console that contains signaling processing, drive, and timing and control mechanisms for appropriate inflation and deflation. The physiological effect of the pump is to improve coronary blood flow and systemic circulation by augmenting aortic root pressure during ventricular diastole at the time of maximum blood flow and reducing the workload of the heart by decreasing the amount of residual blood in the aortic arch, thereby decreasing resistance to the flow of blood from the ventricle.

Figure 6:
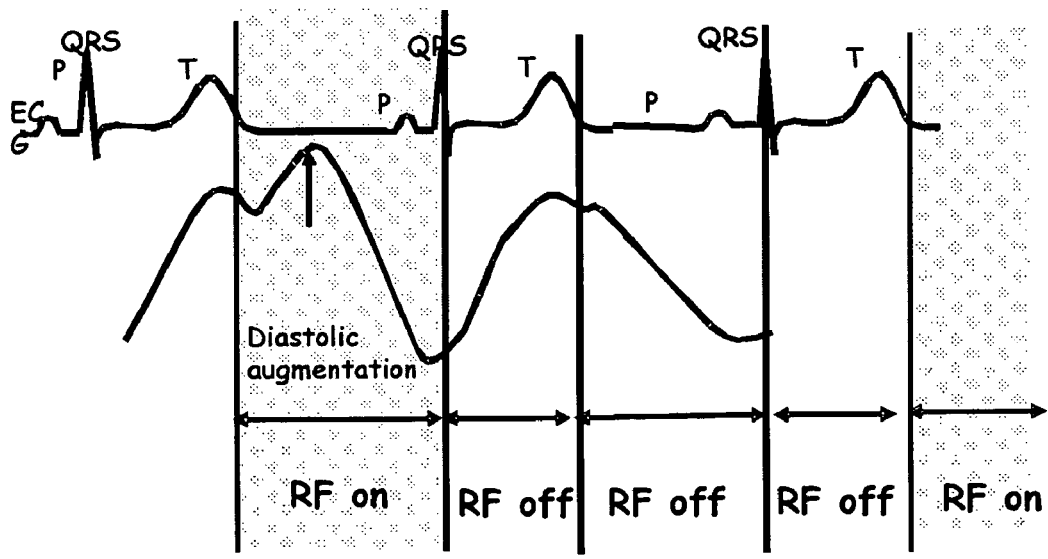
FIG. 6 is a diagram of pulsed RF gated to intra-aortic balloon pump pressure tracings.

In such control systems, automated timing algorithms are known to allow effective balloon pumping, inflation, and depletion during the heart cycle. Thus, in some embodiments, without limitation, in conjunction with operation of the IABP, one may track with some precision the status of PQRST cycle and apply RF current at the appropriate time, including without limitation, in association with the dicrotic notch. (FIG. 6).

In various preferred embodiments of the invention, without limitation, the user may hold the power of the RF current steady while varying the timing of current application. This approach leads to more rapid temperature increases in the tissue. In other embodiments, the power of the RF current may be varied along with the timing of current application, as one example only and without limitation, according to control algorithms known or obvious to those of ordinary skill such that the tissue heat builds up variably.

The present invention overcomes drawbacks in the existing art by leveraging the heat sink effect to support gated or pulsed application of RF current. In accordance with the invention, if one ablates on an artery using delivery of RF current during high periods of blood flow, the risk of damage or other complications in the subject will be minimized or alleviated. Thus, as some examples only, one may apply RF current to the A/V junction, or to a catheter in the coronary sinus in the back of the heart, with decreased risk of complications. In similar fashion, catheter ablation in children may be performed with decreased risk of complications.

In addition, it has been observed that most posteroseptal bypass tracts tend to be located in the regions near the ostium of the middle cardiac vein. Since the posterolateral branch of the right coronary artery is an adjacent structure, ablation in accordance with the existing art here has been complicated by injury to that vessel. However, in accordance with the invention, that risk of injury will minimized. Similarly, the ability to deliver RF energy with minimized risk along the annulus of the tricuspid and mitral valves, in conjunction with catheter ablation of arrhythmogenic foci in the ventricle using an epicardial approach or within the aortic sinus of Valsalva, will all be enhanced through application of gated or pulsed RF current in accordance with the invention. Moreover, in accordance with the invention, the gated or pulsed application of ablative energy at other times may have protective effects on other tissues at risk of unintended damage from the ablative procedure. As one example only, the development of a fistula between the esophagus and the left atrium has been reported as a complication of ablation performed in the posterior left atrium for atrial fibrillation. Esophageal perforation often tends to appear several days or weeks after radiofrequency ablation, suggesting the development of an initial and subacute esophageal wall lesion that may result in esophageal-left atrial fistula rather than an acute perforation directly from the left atrium to the esophagus. Thus, the heat applied to the left atrial endocardium may be causing direct damage to the esophageal arteries, resulting in ischemic damage and necrosis of the esophageal wall. In accordance with the invention, RF or other ablation gated to esophageal blood flow may mitigate or prevent this damage to the esophageal arteries and thus prevent the development of esophageal-LA fistulas by using the heat sink effect. Because the increased period of blood flow in the esophagus will occur during systole, unlike the heart, the timing and gating of RF or other energy application must be adjusted in accordance with the invention so that the energy is applied during systole.

EXAMPLE

The following comprises prophetic examples of some embodiments of the invention, without limitation.

In some embodiments, the invention may comprise:

i) A heart beat detection circuit which traces both electrocardiogram and blood pressure curves, ii) a clock generator which times itself with the heart beat, and iii) a moving position indicator that indicates the delay of RF current application.

A delay circuit with reference to the heart's beat will be generated. With reference to this delay, a gating circuit will be included for the controlling application of RF energy. This system will couple to a source for generation of the radiofrequency energy.

The electrocardiogram and aortic or carotid pressure curves will be displayed on a monitor. A dial-in colored dot will be placeable on one or both of the two curves, and a control knob will be used to position the control to the place on the curve(s) where the user wants the RF current turned on. The QRS complex signal, especially the maximal dV/dt, will be taken to correspond to end-diastole and will be used for gating. This will be used as a circuit trigger to turn RF off. The downstroke of the T wave and the dicrotic notch of the pressure tracing will be usable as triggers to turn RF current on. In some embodiments, two triggers will be used to turn RF on, but only one signal, i.e. the QRS, will be used to turn RF off.

In accordance with the invention, timing of the application of RF energy to the heart's beat will be controlled. In a manual method of operating the system, the heart's rhythm (the PQRST complexes from the ECG tracing and the pressure tracings) will be displayed on a computer display monitor and a dial-in colored dot will be placed on the curve. A rotary knob will be used to position the dot at the place in the cardiac cycle where the operator wishes RF current delivery to commence.

In an automated method, the computer will control and turn on and off the RF energy. There are at least two methods in which the RF energy may be applied. In patients who do not have the IABP, the RF energy will be turned on by the computer monitoring the T Wave and the dicrotic notch in the pressure waveform. In patients with an IABP, the application of RF current may be coupled to the timing and control of the IABP balloon inflations.

The ECG waveform will be monitored by the computer, and the waveform may be stored in a data array. The ECG waveform will be measured by an amplifier. The amplified waveform will be fed into an analog to digital ("A/D") converter. The A/D converter will reside in the computer. The computer will read the A/D converter's output and store it in a running data array. The data will be sampled at about 2 KHz. The reason to sample the data at about 2000 Hertz is that if the signal is contained in a bandwidth of F Hertz, the sampling rate must be twice the maximum frequency of interest. In this example, the rate is about 2000 samples per second.

Next the PQRST curve will be generated for display on the screen in the following way. The data will be continuously filtered digitally with a moving window. The bandwidth of the filter will be chosen at about 10 cycles per second. A peak detection algorithm will be used to detect the first peak, and this will be identified as the QRS curve's peak. The next peak will be determined, and it will be identified as the peak of the T curve. From the start of the T wave the derivative of the pressure wave will be monitored and the maximum of the signal before the next QRS peak will be determined.

A real time clock will run in the background and four complete cycles will be displayed on the monitor. The position of the QRS peak to the next QRS peak will be continuously updated and displayed by a digital readout. The standard deviation for any set number of user chosen cycles will also be displayed digitally. Thus, this embodiment comprises a system that can capture the QRS signal, and while it is understood that the period of the QRS signal is not precise as a clock, its irregularity can be compared to a clock, and the QRS signal will be available in the background as a reference time marker.

In some embodiments, without limitation, a similar scheme is established for the arterial pressure wave. Due to the increased complexity of the arterial waveform, the following procedure will be performed: a Fast Fourier Transformation of the wave will be taken using a period starting with the timing referenced to the QRS peak. The arterial pressure wave's position may move around independent of the ECG wave but we assume that the period of the ECG wave is similar to that of the arterial wave. Therefore, in one example, if the ECG wave is a relatively precise 1 beat per minute, the assumption may be made that the periodicity of the arterial wave is within 10% or 20% of the ECG wave and that it is regular. Thus, there will be two sliding rulers in time, which are understood to relate to two events that must occur in synchrony. Based on this understanding, the QRS timing will be used to time the arterial wave and take again about 2000 samples per second.

Filtering the pressure wave data may be necessary, and the user may generate a Fourier Transformation of the data and locate the peak signals from the Fourier Transformation, thus again determining the peaks. As some examples, 4, 5, or 6 peaks may now correspond to assisted systole, diastolic augmentation, and unassisted systole, and so on. Peak recognition is undertaken and each of the peaks will be recognized. The FFT or Fast Fourier Transform will also generate on the moving data.

In this manner, the peaks of the signals of both the ECG and arterial pressure waveforms will be determined. Markers will be placed on each of these points for the user to observe. One may determine 4 or more peaks in the arterial wave. Once these are shown, in a manual method, the user may observe these and set the system to synchronize itself with any chosen peak and use that as the gating signal. In an automatic method, the machine controls the application of RF energy, and each firing of the RF pulse will also be displayed on the trace in the monitor.

The unassisted systole has a higher pressure reading than the systole in the case of patients with the IABP. In this case, the signals from the IABP device will be used to time the generation of the RF pulse. This can also be automatically done by the computer.

Having identified the peaks in the ECG and curves and knowing where to apply the RF energy, a precise pulse width may be generated next by setting the pulse width using the computer. Function generators are available in the market, and these may be used to gate the RF generator using an RF switch or an RF gating transistor. Alternatively, the RF generator may be a gated oscillator that can generate about 500 KHz, and one can switch it on or off with a precise pulse width. The start of the pulse width can be dialed in and the pulse onset can be synchronized to any section of the curve of the arterial wave. The synchrony can be maintained automatically, and it can be done every other cycle or every cycle.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements. Each of the references identified herein is hereby incorporated by reference as though fully set forth herein.

What is claimed is:

1. A method of treating a cardiac arrhythmia in a mammal, comprising the steps of:
   providing a source of radiofrequency current; and
   administering gated or pulsed radiofrequency current to the mammal during a time period of increased coronary blood flow,
   wherein administering the radiofrequency current begins in association with a fiducial marker of diastole.

2. The method of claim 1, wherein the fiducial marker is electrical diastole.

3. The method of claim 1, wherein administering gated or pulsed radiofrequency current to the mammal during a time period of increased coronary blood flow maximizes a heat sink effect of the coronary blood flow.

4. A method of treating a cardiac arrhythmia in a mammal, comprising the steps of:
   providing a source of radiofrequency current; and
   administering gated or pulsed radiofrequency current to the mammal beginning with the formation of the dicrotic notch in the arterial blood pressure curve of the mammal.

5. The method of claim 4, wherein administering gated or pulsed radiofrequency current to the mammal in association with the formation of the dicrotic notch in the arterial blood pressure curve of the mammal maximizes a heat sink effect of blood flow.

6. A method of treating a cardiac arrhythmia in a mammal, comprising the steps of:
   providing a source of ablative energy; and
   administering gated or pulsed ablative energy to the mammal during a time period of increased coronary blood flow,
   wherein administering the ablative energy begins in association with a fiducial marker of diastole.

7. The method of claim 6, wherein the fiducial marker is electrical diastole.

8. The method of claim 6, wherein administering gated or pulsed ablative energy to the mammal during a time period of increased coronary blood flow maximizes a heat sink effect of the coronary blood flow.

9. A method of treating a cardiac arrhythmia in a mammal, comprising the steps of:
   providing a source of ablative energy; and
   administering gated or pulsed ablative energy to the mammal beginning with the formation of the dicrotic notch in the arterial blood pressure curve of the mammal.

10. The method of claim 6 or claim 9, wherein the ablative energy is microwave, ultrasound, or high intensity focused ultrasound energy.

11. The method of claim 9, wherein administering gated or pulsed ablative energy to the mammal in association with the formation of the dicrotic notch in the arterial blood pressure curve of the mammal maximizes a heat sink effect of blood flow.

* * * * *